United States Patent [19]
Albazi et al.

[11] Patent Number: 6,153,197
[45] Date of Patent: Nov. 28, 2000

[54] TOPICAL TREATMENT OF PSORIASIS

[76] Inventors: Rakhi Albazi; Hermiz Albazi, both of 4344 Moorpark Ave. #1, San Jose, Calif. 95117

[21] Appl. No.: 09/300,813

[22] Filed: Apr. 27, 1999

Related U.S. Application Data

[62] Division of application No. 08/993,548, Dec. 18, 1997, abandoned.
[60] Provisional application No. 60/034,292, Dec. 18, 1996.
[51] Int. Cl.⁷ ..................................................... A61K 35/78
[52] U.S. Cl. ........................................................... 424/195.1
[58] Field of Search ........................................... 424/195.1

[56] References Cited

U.S. PATENT DOCUMENTS 4,181,725   1/1980   Voorhees et al. ...................... 514/297

FOREIGN PATENT DOCUMENTS 842404   7/1960   United Kingdom .

*Primary Examiner*—Jean C. Witz
*Attorney, Agent, or Firm*—James J. Leary; Carol D. Titus

[57] ABSTRACT

A pharmaceutical composition for treatment of psoriasis is a mixture of garlic (*Allium sativum*) and seeds of the radish plant (*Raphanus sativus*) in dilute acetic acid, preferably in the form of white wine vinegar, which is pulverized and blended into a paste. For maximum potency, the composition is preferably prepared immediately before use from fresh ingredients in an amount sufficient for a single treatment. Alternatively, the composition may be prepared ahead of time and stored in a sealed, refrigerated container or otherwise preserved. In the method of treatment, the paste-like composition is applied topically directly to psoriatic plaques on the patient. The composition is allowed to dry on the patient's skin and is left in place for a period of approximately 24 to 72 hours, after which the composition is washed off. The composition is repeatedly applied at intervals of approximately one week over a three to six week period until the desired results are obtained. Typically, the patient's skin will begin to show signs of improvement after the first application of the composition and, after the course of the treatment, the plaque-like lesions will be replaced by healthy, normal skin. The method of treatment is effective on new cases of psoriasis and on long-standing intractable cases of psoriasis, which have not responded to other methods of treatment. Longterm follow-up of patients has shown relatively complete remission of the disease and restoration of normal skin growth for extended periods without recurring symptoms.

21 Claims, No Drawings

TOPICAL TREATMENT OF PSORIASIS

RELATIONSHIP TO OTHER APPLICATIONS

This application is a divisional application of U.S. patent application Ser. No. 08/993,548, which was filed on Dec. 18, 1997, now abandoned, and which claims the benefit of U.S. Provisional Patent Application Ser. 60/034,292, which was filed on Dec. 18, 1996.

FIELD OF THE INVENTION

The present invention relates to a composition and method for topical treatment of skin disorders, in particular, for the treatment of psoriasis.

BACKGROUND OF THE INVENTION

Psoriasis is a chronic skin disease long recognized for its peculiar clinical symptoms characterized by circumscribed red patches covered with white scales, and often accompanied by varying degrees of discomfort. It has been determined that the disease is not contagious; however, its cause and mechanism have not yet been elucidated. See, Kruger, G. G., "*Psoriasis: Current Concepts of its Etiology and Pathogenesis*", The Year Book of Dermatology (1981). Due to the characteristic formation of skin lesions and eruptions, psoriasis gives its victims an unfavorable psychological outlook on life. Among people in Western countries, about 2% of the total population suffer from the disease.

Psoriasis is considered to be a pluricausal hereditary disease whose onset occurs due to the genetic makeup in the body, and which is stimulated by the action of various other factors, such as infection, drugs, food, climate and stress, any one of which can trigger the genetic cause. Since it is known that psoriasis has a close relationship with histocompatibility antigen (HLA) which exhibits polymorphism due to the variation of the HLA gene, it is clear that psoriasis is a hereditary disease.

The occurrence of psoriatic lesions and their remission are often alternately experienced over several years. There are two characteristic symptoms of psoriasis, namely, an inflammatory response common to that caused by other superficial skin diseases and a tendency toward growth of cuticle. Psoriasis is characterized by large, scaly patches of lesions on the skin, which may be reddened and inflamed. Many researchers have sought to elucidate the mechanism of the inflammatory response from the immunological viewpoint and the mechanism of the tendency to abnormal growth of cuticle from the cell physiological viewpoint. However, these mechanisms have not yet been successfully elucidated. See, Beutner, E. H., "*Autoimmunity in Psoriasis*" (CRC Press, Boca Raton, 1982).

Psoriasis is representative of those diseases accompanied by an inflammatory cornification of the skin, and the number of patients suffering from psoriasis is increasing. Various classifications have been proposed for psoriasis, but it is generally classified into psoriasis vulgaris, pustular psoriasis, psoriatic arthritis, guttate psoriasis, and the like. Of these, psoriasis vulgaris is the major type and accounts for 80 to 90% of all instances of the disease. When a person suffers from psoriasis, red maculae or red papules having clear borders occur on portions of the patient's body which are susceptible to external phlogogenic (inflammatory) stimuli, such as the head, elbows, knees and buttocks, and on areas where bacteria and fungi are likely to proliferate, such as pilose (hairy) regions of the body.

Various studies have heretofore been made on psoriasis, including conventional studies directed to the characterization of the morphological changes at the lesion site and more recent studies directed to the characterization of the biochemical and immunological changes at the lesion site. Nevertheless, the essential cause of psoriasis and the mechanism of occurrence of psoriatic lesions have not yet been elucidated. With respect to all types of psoriasis, various symptoms and phenomena are observed, such as hyperplasia and abnormal cornification of epidermal cells ascribed to the excess turnover of the cells by hypermetabolism; asthenia of inflammatory response in the epidermal papillary layer; vasodilation and serpiginous veins in the true skin; and polynuclear leukocyte migration and infiltration into the epidermal cell layers.

Representative of the therapeutic methods heretofore available to physicians seeking to treat psoriasis are the control of the hyperfunctional proliferation of epidermal cells; control of the inflammatory response; promotion of immunomodulation; and avoidance of infection by bacteria and fungi. For example, the following therapeutic methods have conventionally been utilized:

(1) External and internal use of adrenocortical hormone

The external or topical use of a steroid, has the immediate effect of reducing the symptoms of psoriasis, particularly the reduction of eruptions. However, administration of adrenocortical hormone over long periods of time that are necessary in such treatment causes tachyphylaxis, that is, an increased resistance and tolerance buildup, so that the dose must be increased, or stronger drugs must be used in order to obtain a desired therapeutic effect. Occasionally, the occurrence of a new lesion is observed at a site which has been treated with the drug. When adrenocortical hormone is applied to skin in the form of a coating, ointment, salve or paint, the hormone exerts its action not only on the lesion but also on the peripheral normal skin, so that atrophy and achromasia or loss of pigmentation of true skin, or steroid acne, is disadvantageously caused to occur on such areas of the skin.

Further, when the administration of the hormone is interrupted in order to avoid adverse effects of the drugs, withdrawal dermatitis is often caused so that the lesion is likely to expand and deteriorate. Such withdrawal dermatitis is caused particularly when the administration of an internal preparation is discontinued. Accordingly, when the lesion occurs on a relatively large area of skin, the disease cannot be completely cured by this method alone and, therefore, this mode of therapy must be combined with other therapies.

(2) Photochemotherapy

This method consists of administering psoralen in the form of an external or internal preparation and applying longwave ultraviolet rays to the diseased part. However, several types of psoriasis cannot be treated by this method. Moreover, it has the disadvantage in that when it is applied for a long period of time as in the case of heliotherapy, not only is a phenomenon similar to aging of the skin likely to occur, but also a peculiar lentigo or pigmented patch on the skin is likely to be formed.

(3) Phototherapy (UV Irradiation)

As in the case of heliotherapy, when ultraviolet irradiation is carried out for a long period of time, not only is accelerated aging of the skin likely to occur, but also carcinogenesis may be induced.

(4) External use of coal tar

Coal tar suppresses the growth of cells so that the lesion is diminished over a short period of time and a relatively long remission period may be achieved. However, occasionally, stimulant dermatitis and folliculitis (tar acne) may be caused.

(5) Administration of methotrexate

Methotrexate is an antagonist against follic acid, which is active in inhibiting the growth of cells. The use of methotrexate is effective for treating pustular psoriasis. However, the administration of methotrexate for a long period of time causes adverse effects, such as disturbance of liver function and suppression of myeloproliferation.

(6) Administration of retinoid

Retinoid is considered to have an immunomodulation effect, that is, it may control the abnormal cornification of epidermal cells and the hyperfunction of leukocyte migration. The internal administration of retinoid, such as etretinate, is particularly effective for treating pustular psoriasis and psoriatic erythroderma. However, retinoid often exhibits an adverse effect wherein the thickness of skin and visible mucous membrane become small. Further, abnormal levels of serum lipoprotein are occasionally observed. Moreover, retinoid is teratogenic and likely to accumulate and remain inside the body for a long period of time and, therefore, the application of retinoid to a person capable of childbearing is to be avoided. For this reason, retinoid is usually applied only to patients who are beyond childbearing age or who are suffering from intractable psoriasis.

As mentioned above, although the use of adrenocortical hormone exhibits an immediate effect of reducing the symptoms of psoriasis to some extent, tachyphylaxis is likely to occur, making the continued administration of the drug difficult. Further, owing to the tachyphylaxis, the dose must be disadvantageously increased. In such a case, when the administration is stopped in order to halt or avoid adverse effects, the symptoms may often become more severe due to the onset of withdrawal dermatitis. Accordingly, it is difficult to treat psoriasis effectively by the use of adrenocortical hormone alone. With respect to the other therapeutic methods, such as the photochemotherapy and therapy using an epidermal cell growth inhibitor such as coal tar, anthralin, methotrexate and retinoid, when these methods are used in combination with adrenocortical hormone, a therapeutic effect may be attained to some extent, but the psoriasis cannot be truly cured. See, Roenigk, H. H., Jr., and Maibach, H. I., "*Psoriasis*" (Marcel Dekker, New York, 1982).

SUMMARY OF THE INVENTION

The objective of the present invention is to provide a new pharmaceutical composition and a method for its use in the topical treatment of psoriasis and related skin disorders that is effective to reduce or eliminate the scaling and discomfort due to the disease and to restore normal skin growth for extended periods without recurring symptoms. At the same time, it is an important objective that the new treatment avoid the drawbacks of known treatments for psoriasis. In particular, it is an objective of the invention to eliminate undesirable systemic effects, tachyphylaxis or tolerance buildup and side effects, which can result from known treatments.

In keeping with these objectives, in a first aspect, the present invention takes the form of a pharmaceutical composition which is a mixture of effective amounts of garlic (*Allium sativum*) and seeds of the radish plant (*Raphanus sativus*) in dilute acetic acid, which is preferably in the form of white wine vinegar. The mixture is pulverized and blended into a paste, using a laboratory homogenizer or a similar instrument, such as a household kitchen blender. For maximum potency, the composition is preferably prepared immediately before use from fresh ingredients in an amount sufficient for a single treatment. However, it has been found that the composition maintains its potency and effectiveness for several weeks when prepared ahead of time and stored in a sealed, refrigerated container. In a second aspect of the invention which encompasses the method of treatment, the paste-like composition is applied topically directly to the psoriatic plaques on the patient. The composition is allowed to dry on the patient's skin and is left in place on the patient's skin for a prescribed period, which is typically 24 to 72 hours. After 24 to 72 hours, or when the composition begins to peel off of the patient's skin of its own accord, the patient may wash or shower to remove the remainder of the composition. The composition is repeatedly applied in this manner at intervals of approximately one week until the desired results are obtained. A typical treatment regimen may include three to six applications of the composition over a three to six week period. Longer courses of treatment may be needed for more severe cases of psoriasis.

Typically, the patient's skin will begin to show some signs of improvement when the first application of the composition is washed off of the skin and, after the course of the treatment, the plaque-like lesions will be replaced by healthy, normal skin. This method of treatment has been found to be effective on both new cases of psoriasis and on long-standing intractable cases of psoriasis which have not responded to other methods of treatment. Longterm followup of patients has shown relatively complete remission of the disease and restoration of normal skin growth for extended periods without recurring symptoms.

DETAILED DESCRIPTION OF THE INVENTION

The present invention encompasses a new pharmaceutical composition and a method for its use in the topical treatment of psoriasis and related skin disorders. In a first aspect of the invention, the pharmaceutical composition is, in its simplest form, a mixture of garlic (*Allium sativum*) and the seeds of the radish plant (*Raphanus sativus*) in dilute acetic acid (3–5%), which is preferably in the form of white wine vinegar. For maximum potency, the composition is preferably prepared immediately before use from fresh ingredients in an amount sufficient for a single treatment. The total amount of the composition prepared and the ratios of the ingredients in the mixture are somewhat variable, but a typical mixture for application to a small area of psoriatic lesions would consist of approximately 10 grams of garlic (*Allium sativum*), or approximately four average cloves of garlic, and approximately 10 grams of seeds from the radish plant (*Raphanus sativus*) in approximately 25–50 cc of white wine vinegar (3–5% acetic acid). Other variations of the composition would preferably include approximately 0–90% of garlic (*Allium sativum*), 10–90% of seeds from the radish plant (*Raphanus sativus*) and approximately 0–90% of dilute acetic acid by weight. Distilled water may be added to the composition to create a paste-like consistency, if needed. The garlic used in the composition may be of the common variety or the larger elephant garlic variety. It is believed that the most effective varieties of radish seeds for use in the composition are from radish varieties which produce red-colored, spherical roots, such as the varieties known as Cherry Belle, Crimson Giant, Champion or Scarlet Globe radishes. The fresh garlic cloves are peel and placed in a laboratory homogenizer or a similar instrument, such as a household kitchen blender, along with the radish seeds and sufficient white wine vinegar to create a paste-like consistency. The mixture is pulverized and blended at high speed to create a smooth paste. Alternatively, each of the solid ingredients may be ground or pulverized separately and then mixed together, along with the liquid ingredients, to form the final composition. For maximum effectiveness, the composition should be used immediately after mixing, however, it has been found that the composition maintains its potency and effectiveness for several weeks when prepared ahead of time and stored in a sealed, refrigerated container.

It is also anticipated that the potency of the pharmaceutical composition may be preserved for longer periods using other preservation techniques, such as freezing, dehydration, freeze drying or lyophilization. In order to preserve the precise active ingredients of the composition and their interaction with one another, it may be advantageous to preserve the individual ingredients separately, using one or a combination of known preservation techniques, and to combine the ingredients at the point of use. As some patients may find the pungent garlic odor of the composition objectionable when applied topically, the present invention also encompasses the use of deodorized garlic compounds in place of the fresh, whole garlic in the composition. Several commercial deodorized garlic compounds are currently available.

Other variants of the pharmaceutical composition may include inert liquid, cream or paste consistency vehicles to facilitate application of the composition or emollients for softening and moisturizing the psoriatic lesions and the surrounding tissue. The inert ingredients can also be used as diluents to create extra-strength, medium-strength and low-strength variants of the composition for use in different seventies of the disease. Other active ingredients may be added to relieve the itching or discomfort of the lesions or to provide a combined therapeutic effect or a synergistic effect with the principle ingredients.

In a second aspect of the invention, the pharmaceutical composition described above is used in a method for topical treatment of psoriasis and related skin disorders. To begin the method, the psoriatic lesions are swabbed with white wine vinegar (3–5% acetic acid) or the like. Then, the paste-like composition is applied topically directly to the moistened psoriatic lesions, using a small spatula, tongue depressor or similar applicator. The entire lesion should be covered with a thin layer of the composition. Testing to date has not shown any adverse effect from the composition to the native skin surrounding the lesion, however, it is recommended that the application of the composition be limited to the lesion and its periphery. The patient may experience a mild burning sensation when the composition is applied, especially if the lesions are raw or irritated. The composition is allowed to dry on the patient's skin and is left in place on the patient's skin for a prescribed period, which is preferably from approximately one hour to one week, more preferably from approximately 24 to 72 hours. The applied composition may be left uncovered, or it may be covered with a loose cloth bandage for cosmetic reasons. The patient should be instructed not to scratch, peel or wash off the composition during the prescribed period. After the prescribed period (typically 24 to 72 hours) or after the composition has peeled off of the patient's skin of its own accord, the patient may wash or shower to remove the remainder of the composition.

The composition is repeatedly applied in this manner at intervals, which are preferably from approximately one day to one month, more preferably approximately one week, until the desired results are obtained.

A typical treatment regimen may include three to six applications of the composition over a three to six week period. Longer courses of treatment may be needed for more severe cases of psoriasis. Typically, the patient's skin will begin to show some signs of improvement when the first application of the composition is washed off of the skin and, after the course of the treatment, the plaque-like lesions will be replaced by healthy, normal skin. This method of treatment has been found to be effective on both new cases of psoriasis and on long-standing intractable cases of psoriasis which have not responded to other methods of treatment. Longterm follow-up of patients has shown relatively complete remission of the disease and restoration of normal skin growth for extended periods without recurring symptoms. The treatment has also been found to be free of undesirable systemic effects, tolerance buildup and side effects, which can result from known treatments.

A number of clinical trials have been done on human volunteers to demonstrate the efficacy of this treatment. The following are given as examples of the efficacy of treatment for severe, intractable cases of psoriasis, as well as new cases of psoriasis.

Example A—A male patient with large, scaling patches of psoriatic lesions over 40–50% of his body underwent treatment using the pharmaceutical composition and the method of the present invention. The patient had previously undergone treatments using both prescription and over-the-counter remedies with only temporary reduction in the degree of scaling. Over the course of the treatment, the patient experienced over 95% remission of the disease symptoms and, in longterm follow-up, the patient has been free of recurrence of the disease except for one small patch of scales.

Example B—A female patient with scaling patches of psoriatic lesions over 10% of her body underwent treatment using the pharmaceutical composition and the method of the present invention. The patient had no previous medical treatments for the psoriasis. Over the course of the treatment, the patient experienced 100% remission of the disease symptoms and no recurrence of the disease in longterm follow-up.

Clinical trials such as these have shown that the composition and method of treatment of the present invention are effective to provide rapid relief from symptoms in both new cases of psoriasis and longstanding intractable cases of psoriasis which have not responded to other methods of treatment. In addition, longterm follow-up of patients has shown relatively complete remission of the disease and restoration of normal skin growth for extended periods without recurring symptoms. The precise active ingredients of the composition and their interactions with one another and the exact biological mechanisms that lead to relief of symptoms and longterm remission of the disease are not fully understood at this time and are the subjects of ongoing investigations. However, it is hypothesized at this time that the therapeutic action of the composition may be a result of a synergistic combination between allicin, which is produced upon pulverization of the garlic (*Allium sativum*), and various calmodulin antagonists, which have recently been identified as being present in the seeds of the radish plant (*Raphanus sativus*). Another contributing mechanism of the composition may be as a counterirritant that may deplete substance P or other substances in the tissues, which play a role in the inflammatory response. Consequently, effective variations of the composition may be produced using combinations of allicin, which may be derived from garlic (*Allium sativum*) or artificially synthesized, calmodulin antagonists, which may be derived from the radish plant (*Raphanus sativus*) or its seeds or artificially synthesized, and/or counterirritant substances, which may be synthesized or derived from either. The composition of the present invention may also find application for treatment of other skin conditions, as well as other proliferative diseases in other tissues of the body. Thus, the scope the present invention should not be limited to the specific examples given, but should be determined by the following claims and their legal equivalents.

What is claimed is:

1. A method for topical treatment of psoriasis comprising applying to a psoriatic lesion a pharmaceutical composition comprising:

pulverized seeds of a radish plant (*Raphanus sativus*);

pulverized garlic cloves (*Allium sativum*); and dilute acetic acid.

2. The method for topical treatment of psoriasis of claim 1, further comprising repeatedly applying said pharmaceutical composition to the psoriatic lesion at intervals until the psoriatic lesion goes into remission.

3. The method for topical treatment of psoriasis of claim 1, further comprising swabbing the psoriatic lesion with dilute acetic acid prior to applying said pharmaceutical composition to the psoriatic lesion.

4. The method for topical treatment of psoriasis of claim 1, further comprising allowing said pharmaceutical composition to remain on the psoriatic lesion for a period of approximately 24 to 72 hours.

5. The method for topical treatment of psoriasis of claim 4, further comprising removing said pharmaceutical composition from the psoriatic lesion after the period of approximately 24 to 72 hours.

6. The method for topical treatment of psoriasis of claim 5, further comprising repeatedly applying said pharmaceutical composition to the psoriatic lesion at intervals until the psoriatic lesion goes into remission.

7. The method for topical treatment of psoriasis of claim 5, further comprising repeatedly applying said pharmaceutical composition to the psoriatic lesion, and allowing said pharmaceutical composition to remain on the psoriatic lesion for a period of approximately 24 to 72 hours prior to removing the composition from the psoriatic lesion, at approximately one week intervals for a period of approximately three to six weeks.

8. A method for topical treatment of psoriasis comprising: forming a treatment composition by:

pulverizing seeds of a radish plant (*Raphanus sativus*);

pulverizing garlic cloves (*Allium sativum*); and mixing the pulverized seeds of the radish plant (*Raphanus sativus*) and the pulverized garlic cloves (*Allium sativum*) together with dilute acetic; and applying said treatment composition to a psoriatic lesion.

9. The method for topical treatment of psoriasis of claim 8, further comprising repeatedly applying said treatment composition to the psoriatic lesion at intervals until the psoriatic lesion goes into remission.

10. The method for topical treatment of psoriasis of claim 8, further comprising swabbing the psoriatic lesion with dilute acetic acid prior to applying said treatment composition to the psoriatic lesion.

11. The method for topical treatment of psoriasis of claim 8, further comprising allowing said treatment composition to remain on the psoriatic lesion for a period of approximately 24 to 72 hours.

12. The method for topical treatment of psoriasis of claim 11, further comprising removing said treatment composition from the psoriatic lesion after the period of approximately 24 to 72 hours.

13. The method for topical treatment of psoriasis of claim 12, further comprising repeatedly applying said treatment composition to the psoriatic lesion at intervals until the psoriatic lesion goes into remission.

14. The method for topical treatment of psoriasis of claim 12, further comprising repeatedly applying said treatment composition to the psoriatic lesion, and allowing said treatment composition to remain on the psoriatic lesion for a period of approximately 24 to 72 hours prior to removing said treatment composition from the psoriatic lesion, at approximately one week intervals for a period of approximately three to six weeks.

15. The method for topical treatment of psoriasis of claim 8, wherein said dilute acetic acid comprises white wine vinegar.

16. The method for topical treatment of psoriasis of claim 8, wherein said seeds of the radish plant (*Raphanus sativus*) and said garlic cloves (*Allium sativum*) are pulverized together in said dilute acetic acid.

17. The method for topical treatment of psoriasis of claim 8, wherein said pulverized seeds of the radish plant (*Raphanus sativus*) and said pulverized garlic cloves (*Allium sativum*) are mixed together in approximately equal amounts by weight, with a sufficient amount of said dilute acetic acid to create a paste.

18. A pharmaceutical composition for topical treatment of psoriasis comprising:

pulverized seeds of a radish plant (*Raphanus sativus*);

pulverized garlic cloves (*Allium sativum*); and dilute acetic acid.

19. The pharmaceutical composition for topical treatment of psoriasis of claim 18, wherein said dilute acetic acid comprises white wine vinegar.

20. The pharmaceutical composition for topical treatment of psoriasis of claim 18, wherein said seeds of the radish plant (*Raphanus sativus*) and said garlic cloves (*Allium sativum*) are pulverized together in said dilute acetic acid.

21. The pharmaceutical composition for topical treatment of psoriasis of claim 18, wherein said pulverized seeds of the radish plant (*Raphanus sativus*) and said pulverized garlic cloves (*Allium sativum*) are mixed together in approximately equal amounts by weight, with a sufficient amount of said dilute acetic acid to create a paste.

* * * * *